United States Patent [19]

Janoff et al.

[11] Patent Number: 5,364,631

[45] Date of Patent: Nov. 15, 1994

[54] TOCOPHEROL-BASED PHARMACEUTICAL SYSTEMS

[75] Inventors: Andrew S. Janoff, Yardley, Pa.; Lawrence Boni; Sharma R. Minchey, both of Monmouth Junction, N.J.; Lois E. Bolcsak, Lawrenceville, N.J.; Steven J. Weiss, Belle Mead, N.J.

[73] Assignee: The Liposome Company, Inc., Princeton, N.J.

[21] Appl. No.: 18,913

[22] Filed: Feb. 17, 1993

Related U.S. Application Data

[63] Continuation of Ser. No. 259,988, Oct. 19, 1988, abandoned, which is a continuation-in-part of Ser. No. 110,261, Oct. 19, 1987, abandoned.

[51] Int. Cl.$^5$ ............................................. A61K 9/127
[52] U.S. Cl. .................................... 424/450; 264/4.1; 264/4.6; 428/402.2
[58] Field of Search ................................. 428/402.2

[56] References Cited

U.S. PATENT DOCUMENTS

| | | | |
|---|---|---|---|
| 3,608,073 | 9/1971 | Phares et al. | 424/168 |
| 3,993,754 | 11/1976 | Rahman et al. | 424/177 |
| 4,145,410 | 3/1979 | Sears et al. | 424/19 |
| 4,224,179 | 9/1980 | Schneider et al. | 252/316 |
| 4,229,360 | 10/1980 | Schneider et al. | 260/403 |
| 4,235,871 | 11/1980 | Papahadjopoulos et al. | 424/19 |
| 4,522,803 | 6/1985 | Lenk et al. | 424/1.1 |
| 4,588,578 | 5/1986 | Fountain et al. | 424/1.1 |
| 4,670,185 | 6/1987 | Fujiwara et al. | 264/4.1 |
| 4,721,612 | 1/1988 | Janoff et al. | 424/1.1 |
| 4,743,449 | 5/1988 | Yoshida et al. | 424/420 |
| 4,861,580 | 8/1989 | Janoff et al. | 424/1.1 |
| 4,880,635 | 11/1989 | Janoff et al. | 424/1.1 |

FOREIGN PATENT DOCUMENTS

| | | |
|---|---|---|
| 0241573 | 4/1986 | European Pat. Off. |
| 0220797 | 7/1986 | European Pat. Off. |
| 85/00968 | 3/1985 | WIPO |
| 85/04578 | 10/1985 | WIPO |
| 86/00238 | 1/1986 | WIPO |
| WO86/01103 | 2/1986 | WIPO |
| 87/00043 | 1/1987 | WIPO |
| 87/02219 | 4/1987 | WIPO |
| WO87/02219 | 4/1987 | WIPO |

OTHER PUBLICATIONS

Bangham, M., et al., "Diffusion of Univalent Ion Across the Lamellae of Swollen Phospholipids"; 1965; J. Biol. Chem., 12:238–252.

Chrai, S., et al., "Ocular Evaluation of Methylcellulose Vehicle in Albino Rabbits"; 1974; J. Pharm. Sci., 63:1218–1223.

Chung, P., et al., "Kinetics of the Hydrolysis of Pilocarpine in Aqueous Solution"; 1970; J. Pharm. Sci., 59(9):1300–1305.

Lai, M., et al., "Effects of Replacement of the Hydroxyl Group of Cholesterol and Tocopherol on the Thermotropic Behavior of Phospholipid Membranes"; 1985; Biochemistry, 24:1646–1661.

Lee, M., et al., "Corneal Absorption of Ophthalmic Drugs"; 1974; J. Pharm. Sci., 63:721–724.

Papahadjopoulos, D., et al., "Phospholipid Model Membranes"; 1967; Biochim. Biophys. Acta., 135:624–638.

Benita et al., Pilocarpine hydrochloride liposomes: characterization in vitro and preliminary evaluation in vivo in rabbit eye; 1984, J. Microencapsulation, vol. 1, No. 3, 203–216.

*Primary Examiner*—G. S. Kishore
*Attorney, Agent, or Firm*—Joanne L. Feeney

[57] ABSTRACT

A method for making a pharmaceutical composition is described. The composition is comprised of an organic acid derivative of alpha tocopherol, and may additionally comprise other lipids. The composition may be in the form of liposomes, and as such are associated with or entrap a bioactive agent. Particularly suited for such systems are drugs stable at acidic pH, for example drugs having imidazole groups, such as pilocarpine. The composition requires a stabilizer to maintain the bilayer phase of the organic acid derivative of alpha tocopherol in a low pH environment. Such a stabilizer is for example a detergent. Upon in vivo administration of the system and concomitant increase of pH, viscosity of the preparation increases.

27 Claims, No Drawings

TOCOPHEROL-BASED PHARMACEUTICAL SYSTEMS

RELATED COPENDING U.S. APPLICATION DATA

This application is a continuation of copending application Ser. No. 07,259,988 filed on Oct. 19, 1988, now abandoned, which is a continuation-in-part of copending U.S. patent application Ser. No. 110,261, filed Oct. 19, 1987.

BACKGROUND OF THE INVENTION

The present invention is related to stable liposome compositions. More particularly, the invention is directed to the physical stabilization of organic acid derivatives of alpha tocopherol bilayers comprising stabilizer, for use as a pharmaceutical composition.

The salt forms of organic acid derivatives of alpha tocopherol, such as tris (tris(hydroxymethyl)aminomethane)-tocopherol hemisuccinate (t-THS) are known to form closed multilamellar vesicles with high trapping efficiencies and captured volumes at physiological pH values (Janoff et al., U.S. patent application Set. No. 911,138, filed Sep. 24, 1986, entitled "Alpha Tocopherol-Based Vesicles", and incorporated herein by reference; and Lai et al., 1985, Biochemistry, 24:1646-1661). THS also demonstrates polymorphic (e.g. bilayer to hexagonal$_{II}$) phase behavior dependent upon pH or the presence of divalent cartons. For example, while aqueous suspensions of THS are in the bilayer phase at physiological pH and above (about pH 6.0-9.0), lowering the pH below about 6.0 or introducing divalent cartons such as Mg$^{++}$ or Ca$^{++}$ produces vesicle aggregation and fusion, and induces hexagonal phase (hex$_{II}$) formation.

Neither the tocopherol acid succinate (hemisuccinate) nor the tris salt form of THS form or remain liposomes at acidic pH, this due to the formation of hex$_{II}$ structures at low pH. Alpha-THS is a branched single chain lipid that differs dramatically in structure from other lipids known to exhibit bilayer to hexagonal phase polymorphism, such lipids being for example, phosphatidylethanolamine, cardiolipin, and mono-diacyl glycerides.

In previous studies using alpha tocopherol hemisuccinate (THS) in liposomal drug delivery systems, the bioactive agent to be entrapped or associated with the THS was stable at physiological pH values. In such drug delivery systems, the requirements for physiological pH for bilayer state of THS was met by the similar pH requirements for the drug. However, certain drugs, for example pilocarpine, are catalytically active in such unprotonated form as at physiological pH, and therefore require delivery systems of more acidic pH. Such a system heretofore was not compatible with THS as the delivery system, due to the pH requirements of THS in the bilayer state, since such conditions make THS highly susceptible to hydrolysis and therefore degradation. Moreover, pilocarpine itself is unstable at high pH where it undergoes base-catalyzed hydrolysis. At lower pH, pilocarpine is protonated and more stable (Chung et al., 1970, *J. Pharm. Sci.*, 59(9):1300-1305). Pilocarpine among other drugs thus requires, and is therefore preferably associated with bilayer systems at lower (acidic) pH.

Thus, in lipid-based delivery systems employing THS and drugs such as pilocarpine, the requirement for acidic conditions of the drug appears incompatible with the requirement for the bilayer form (neutral to basic conditions) for the THS. Due to the polymorphic phase behavior of the THS molecule, which produces the above-mentioned hex$_{II}$ phase and precipitation in solution at acidic pH, and the requirement for acidic pH of the drug, we have developed a new system utilizing stabilizers that maintain the bilayer configuration of the THS at both acidic and alkaline pH. Under these conditions, where stabilizer is present, the THS is stabilized in solution at acidic pH. This system utilizes THS liposomes which associate with or entrap bioactive agent which tolerate or require low pH conditions, for example, drugs having imidazole groups, where the final pH of the preparation is acidic.

Stabilizers are defined as compounds which allow the formation and/or maintenance of the bilayer state of d-alpha-tocopherol acid succinate based liposomes in an acidic pH environment. Materials which have been found to perform that function generally belong to the classes of compounds commonly known as surfactants and detergents. In the present invention, stabilizers (detergents) such as the pharmaceutically acceptable excipients polyoxyethylene alkyl ethers (such as polyoxyethylene-4-laurel ether, polyoxyethylene-23-laurel ether, and a combination thereof, known also by the respective names Laureth-4, Laureth-23, and Laureth-12, ICI Americas, Inc.); the appended numbers denoting the average number of ethylene oxide units in the polyethylene glycol segment), were found to stabilize THS into the bilayer phase at acidic pH.

We have surprisingly discovered a system using THS-stabilizer bilayers which may be adjusted to acidic pH, thereby accomodating drugs that require low pH conditions. In this system, a THS-stabilizer bilayer is formed at low pH, for example at acidic pH, for example at between about pH 2.0 and 6.5, more preferably about pH 4.0-5.0, most preferably about pH 4.5. A drug requiring such low pH conditions may then be added to the preparation; alternatively, the drug may be added prior to adjustment of the pH. We have further discovered that when this preparation was adjusted to neutral pH (e.g., physiological pH), the bilayer phase of the system is preserved, and the viscosity of the solution may increase. Such pH adjustment may effectively take place upon addition of the solution to body fluids, e.g. in the case of ocular pilocarpine and the tear film. For example, addition of the acidic liposomal THS pilocarpine solution to the eye results in an increase in viscosity which may increase the time the pilocarpine is in contact with the eye tissues. An increase in contact time is known to be directly related to the enhanced uptake of drugs by the eye tissues (Chrai et al., 1974, *J. Pharm. Sci.*, 63:1218, Lee at al., 1974, *J. Pharm. Sci.*, 63:721).

The mode of delivery of the bioactive agent of the present invention is preferably via association of the agent with lipid, (e.g., THS), via entrapment in the liposome, association with the outside of the liposome, or inside the lipid bilayer. Liposomes are completely closed lipid bilayer membranes containing an entrapped aqueous volume. Liposomes may be unilamellar vesicles (possessing a single membrane bilayer) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient towards the center of the bilayer while the hydrophilic "heads" orient towards the aqueous phase.

The original liposome preparation of Bangham et al. (J. Mol. Biol., 1965, 12:238-252) involves suspending phospholipids in an organic solvent which is then evaporated to dryness leaving a phospholipid film on the reaction vessel. Next, an appropriate amount of aqueous phase is added, the mixture is allowed to "swell," and the resulting liposomes which consist of multilamellar vesicles (MLVs) are dispersed by mechanical means. This technique provides the basis for the development of the small sonicated unilamellar vesicles described by Papahadjopoulos et al. (Biochim. Biophys. Acta., 1968, 135:624-638), and for large unilamellar vesicles.

As mentioned above, a variety of sterols and their water soluble derivatives have been used to form liposomes; see specifically Janoff et al., PCT Publication No. 85/04578, Oct. 24, 1985, entitled, "Steroidal Liposomes." Mayhew et al., PCT Publication No. 85/00968, Mar. 14, 1985, described a method for reducing the toxicity of drugs by encapsulating them in liposomes comprising alpha-tocopherol and certain derivatives thereof. In a liposome-drug delivery system, a bioactive agent such as a drug is entrapped in or associated with the liposome and then administered to the patient to be treated. For example, see Rahman et al., U.S. Pat. No. 3,993,754; Sears, U.S. Pat. No. 4,145,410; Papahadjopoulos et al., U.S. Pat. No. 4,235,871; Schnieder, U.S. Pat. No. 4,114,179; Lenk et al., U.S. Pat. No. 4,522,803; and Fountain et al., U.S. Pat. No. 4,588,578.

The present invention solves the problem of delivery of an acid requiring or acid tolerating drug at acidic pH, with THS. By combining THS with stabilizer at an acidic pH, bilayer conditions of THS are preserved. Further, following the adjustment of the pH to neutral, the system increases in viscosity, enhancing the contact time between drug and body tissue. The system may also comprise a drug, such as an acid requiring or acid tolerating drug, for example, pilocarpine.

In the present invention, liposomes comprising the THS, bioactive agent, and stabilizer are adjusted to acidic pH and administered to a subject.

SUMMARY OF THE INVENTION

The present invention discloses a method for sustaining action of drugs requiring or tolerating low pH conditions, wherein an organicacid derivative of alpha tocopherol is mixed with a stabilizer at acidic pH. The resulting mixture may additionally comprise a bioactive agent. This method is used where the bioactive agent is a drug which undergoes base catalyzed hydrolysis and therefore requires or tolerates low pH conditions. Such a drug is, for example, a drug with an imidazole group, such as pilocarpine.

In the preferred embodiments of the invention, the stabilizer is a detergent, such as a polyoxyethylene alkyl ester or ether, such as Laureth-12, Laureth-23, or tocopherol polyoxyethylene glycol succinate (TPGS). The stabilizer, if it is lipophilic, can be combined with the organic acid derivative of alpha tocopherol in an organic solvent such as methylene chloride. An aqueous suspension comprising the bioactive agent, and a buffer may be admixed with the organic solution, and the organic solvent removed. The pH of the resulting suspension is then adjusted to about 3.0-5.5, more particularly about 4.5. The preparation additionally comprises preservative, such as p-hydroxybenzoic acid esters, benzyl alcohol, benzylkonium chloride, or sorbic acid.

Thus, the invention is directed to a sustained action liposome composition comprising an organic acid derivative of alpha tocopherol and a stabilizer at low pH at the conditions mentioned above. The composition may be a pharmaceutical composition which contains a bioactive agent, for example, an ocular affliction-treating effective amount of pilocarpine, and which may be administered topically by applying the product to the ocular tissues of a subject in need of such treatment.

Any of several methods can be used in the formation of the low pH THS stabilized liposomes of the invention. One method for forming the composition of the invention is to associate a drug requiring low pH with liposomes comprising an amphipathic compound (THS) requiring physiological pH, by dissolving the drug in an aqueous solution at low pH, suspending the THS in an organic solvent comprising a stabilizer, combining the first solution with the suspension above, removing the organic solvent, and adjusting the pH. The organic solvent used is preferably methylene chloride.

Using any of the methods of the invention, a drug delivery system comprising tocopherol hemisuccinate and a stabilizer is produced, wherein the pH of the system is acidic.

The liposomes may be administered topically to the eye.

DETAILED DESCRIPTION OF THE INVENTION

The present invention is directed to compositions and methods for producing organic acid derivatives of alpha tocopherol based systems, which are particularly suitable for the delivery of bioactive agents unstable at physiological pH and requiring or tolerating a low pH (acidic) environment for stability. More particularly, the invention relates to a method for co-stabilizing the organic acid derivatives of alpha tocopherol and acid-requiring bioactive agent (particularly drugs such as, for example, those having imidazole groups, such as pilocarpine) in bilayers. Such stabilization requires a stabilizer such as a surfactant and/or detergent, most preferably a detergent such as the polyoxyethylene alkyl ethers or esters. Such organic acid derivatives of tocopherol bilayer-forming compounds is tocopherol hemisuccinate (THS).

Characterizing the pH-dependent polymorphic nature of the THS is of importance in designing drug delivery systems comprising THS. Freeze fracture electron microscopy performed on THS bilayers (liposomes) to determine the effect of pH on the THS phase behavior demonstrated that at pH 7.0, THS forms a heterogenous population of multilamellar and unilamellar vesicles. Alternatively, liposomes made with pilocarpine-THS at pH 7.0 are aggregated multilamellar liposomes, heterogenous with regard to both size and shape. It is known that pilocarpine and THS are chemically unstable in mixtures at pH values around 7.0.

The macroscopic differences observed between THS preparations and pilocarpine-THS preparations suggest an association between the pilocarpine and the THS. Upon lowering the pH of both preparations, precipitates resembling hex$_{II}$phase lipid are formed. The fact that the precipitates appear similar upon acidification indicates a loss of the pilocarpine association of THS at the lower pH. Such polymorphic (bilayer to hex$_{II}$) phase behavior of THS at low pH makes difficult or unsuccessful the co-administration of drugs whose stability profile requires (or tolerates) low pH.

We have found that the incorporation of certain stabilizer molecules such as a detergent, in the liposome preparation prevents the formation of the hex$_{II}$ structures and thus stabilizes the preparation. The necessity of an acidic pH environment for the drug is thus made possible by the inclusion of the stabilizer into the THS preparation, and thus an acid requiring drug may be delivered via the THS system.

The methods of the present invention enable administration of such acid-requiring drugs with THS liposomes, thus stabilized. The THS combined with the stabilizer (surfactant or detergent) thus constitutes a new system for delivery of such drugs. The association of the drug with this delivery system enables sustained action of the drug while presenting conditions under which the drug is most stable. Furthermore, the adjustment of the pH to neutral values, upon in vivo administration, may increase the viscosity of the system thereby enhancing the contact time of the system with the tissues.

Formulations of the present invention can be prepared by admixing an organic and an aqueous phase; the organic phase comprises THS and the stabilizer (if the stabilizer used is lipophilic, and therefore soluble in organic solvent) in an organic solvent such as methylene chloride. This method promotes the formation of a bilayer structure at the outset, which tends to remain bilayer after further adjustments to pH. This solution is in a physically stable bilayer phase, and drug may be added to it at a later time.

The aqueous phase can comprise a preservative antimicrobial agent, such as sorbic acid, and an antimicrobial agent enhancer, such as EDTA, which are mixed in sterile water or buffer and heated to dissolve. Depending upon the preservative employed, the heating step may be omitted. After cooling, the drug (pilocarpine) is added to the aqueous preservative solution. This aqueous solution should contain enough buffer salts or acid or base equivalents such that the final preparation, after admixture with the organic phase, is at or about pH 4.5. Only minor adjustments to the pH of the resulting preparation, after removal of the solvent, should be made with a base such as sodium hydroxide (NaOH), to about pH 4.5.

The THS (organic phase) can then be admixed with the bioactive agent (aqueous phase) and the suspension hand mixed. The organic solvent is then removed, for example, by evaporation under vacuum. After this time, the resulting solution is adjusted to the desired volume with sterile distilled water or buffer, and the pH adjusted to about 4.5, using salts, dilute base, dilute acids, such as sodium citrate or citric acid.

If the stabilizer employed is hydrophilic, it can be mixed with the aqueous rather than the organic phase.

The resulting pilocarpine-THS liposomes can be size reduced or homogenized using the Continuous Size Reduction process disclosed in commonly assigned copending U.S. patent application Ser. No. 036,980, filed Apr. 16, 1987, incorporated herein by reference. In this technique, a liposome solution is passed under pressure a multiple of times (preferably about 10 times) through a stainless steel filter having a nominal pore size of 500 nm. Alternatively, the liposomes may be extruded by passing through a uniform-pore size filter according to the LUVET process, disclosed in Cullis et al., PCT Publication No. 87/00238, Jan. 16, 1986, entitled "Extrusion Technique for Producing Unilamellar Vesicles" incorporated herein by reference. Vesicles made by this technique, called LUVETS, are extruded under pressure through a membrane filter. Vesicles may also be made by an extrusion technique through a 200 nm filter; such vesicles are known as VET$_{200}$s. Alternatively, the liposomes may be homogenized using an apparatus such as the Manton-Gaulin homogenizer.

As used in the present invention, the term bioactive agent is understood to include any compound having biological activity; e.g., drugs and other therapeutic agents such as peptides, hormones, toxins, enzymes, neurotransmitters, lipoproteins, glycoproteins, immunomodulators, immunoglobulins, polysaccharides, cell receptor binding molecules, nucleic acids, polynucleotides, and the like, as well as biological tracer substances such as dyes, radio-opaque agents, and fluorescent agents. In specific, the present invention is directed to drugs that are ocular therapeutic agents, for example, pilocarpine.

For the present invention, the stabilizer is included in amounts dependent on the amount of lipid present, and the biocompatibility of the stabilizer. Preferably, the composition contains about 2–20% stabilizer. A detergent or surfactant does not successfully stabilize the preparation if there is precipitate, crystalline structure, gelling, clumping or other non-homogenous material present in the preparation. At 20% stabilizer, no hex$_{II}$ phase lipid is seen in the preparation, but only liposomes are present, the bilayer being completely stabilized.

Stabilizers that may be used in the invention are those such as detergents or surfactants, for example polyoxyl stearate, octoxynol (Triton 720), or the polyoxyethylene alkyl ethers, such as Laureth-12 and 23, combinations of Laureth-4 and 23, and d-alpha tocopheryl polyethylene glycol 1000 succinate. The following detergents, however, do not stabilize the preparations and therefore are not recommended for use: polyoxyethylene alkyl esters, polyoxyethylene sorbitan, polysorbate 80 (Tween 80), sorbitan monopalmitate or sorbitan monolaurate, glycerol monostearate, tyloxapol, and the poloxamers (Pluronic F-127 and Pluronic F-68).

The antimicrobial preservative solutions that may be used in the present invention include sorbic acid, p-hydroxybenzoic acid methyl, ethyl, butyl, or propyl esters, benzyl alcohol, chlorbutanol, benzylkonium chloride, phenethyl alcohol, and the mercurial preservatives. Sorbic acid is preferably present in the final preparation at about 0.01–0.1% (w/v), most preferably 0.05%, the mercurials at about 0.001–0.004% (w/v), chlorbutanol and phenethyl alcohol at about 0.5% (w/v), and benzylkonium chloride or other quaternary amine preservatives at about 0.01 or below (w/v). The amount of preservative needed can be determined by an antimicrobial effectiveness test (AME) and by its structural and chemical compatibility with other components in the preparation. The preservative solution may also comprise enhancer substances such as ethylenediamine tetraacetic acid (EDTA) at about 0.01–0.1% (w/v), preferably 0.05%. Such substances enhance the antimicrobial activity of the preservative. Preferably in the present invention sorbic acid:EDTA (0.05%: 0.05%) is used.

The aqueous solutions used in the stabilizer-bilayer THS preparations of the invention include but are not limited to distilled water, up to 0.1% (w/v) sorbic acid in water, or up to 0.1% disodium EDTA dihydrate in water. Preferably, sterile water is used. The aqueous phase can also comprise the bioactive agent, stabilizer, preservatives, and buffer salts, as well as acid and bases.

The amphipathic material bilayer-forming substance (lipid) of the present invention comprises a salt form of an organic acid derivative of a tocopherol, or other structurally related compounds, which is capable of forming completely closed bilayers in aqueous solutions. The suitability of a particular salt form of an organic acid derivative of a tocopherol depends upon its ability to sequester a water soluble compound such that the compound is not in contact with the outside environment. Any organic acid derivative of tocopherol, such as, for example, alpha tocopherol hemisuccinate (THS), may be used in the practice of the invention.

Organic acids which can be used to derivatize that tocopherol (for example, the alpha tocopherol), include but are not limited to the carboxylic acids, dicarboxylic acids, polycarboxylic acids, hydroxy acids, amino acids and polyamino acids. Such derivatives may be esters, hemiesters, or ethers. Because the salt forms increase the water solubility of organic acids, any organic acid can be used to derivatize the alpha tocopherol; however an advantage may be obtained if the organic acid moiety itself is water soluble. Such water soluble organic acid moieties include but are not limited to water soluble carboxylic acids such as acetic, propionic, butyric, valeric acids and the like (N,B., up to four-carbon acids are miscible with water; the five carbon free acid is partially soluble and the longer chain free acids are virtually insoluble); water soluble aliphatic dicarboxylic acids such as malonic, succinic, glutaric, adipic, pimelic, maleic, and the like (N,B, the shorter chains are appreciably more soluble in water; borderline solubility in water occurs at $C_6$ to $C_7$); and water soluble aromatic dicarboxylic acids such as hemimellitic, trimesic, succinimide, and the like; polycarboxylic acids; water soluble hydroxy acids such as glycolic, lactic, madelic, glyceric, malic, tartaric, citric, and the like (N,B, alpha-hydroxy acids containing a branched chain attached to the alpha carbon of the carbonyl group would be less susceptible to hydrolysis and therefore advantageous in the practice of the present invention); and any of the amino acids or polyamino acids.

The salt forms of the derivatized alpha tocopherol can be prepared by dissolving both the organic acid derivative of the alpha tocopherol and the counterion of the salt (e.g., the free base of the salt) in an appropriate volatile solvent, and removing the solvent by evaporation or a similar technique leaving a residue which consists of the salt form of the organic acid derivative of alpha tocopherol. Counterions that may be used include but are not limited to tris, 2-amino-2-methyl-1,3-propanediol, 2-aminoethanol, bis-tris propane, triethanolamine, and the like to form the corresponding salt. In the present invention, the free acid form of THS is preferably used.

In the present invention THS is preferably used at 10.2% (w/v) of the final preparation. The preparation may also comprise other lipids such as phospholipids, for example, phosphatidylcholine (PC), phosphatidylethanolamine (PE), phosphatidylserine (PS), phosphatidylglycerol (PG), phosphatidic acid (PA), phosphatidylinositol (PI), sphingomyelin (SPM), and the like. The phospholipids can be synthetic or derived from natural sources such as egg or soy. For example, the THS may be used in a 70:30 molar ratio with egg PC. Additionally, the liposomes may comprise cholesterol hemisuccinate (CHS) with the THS, used in ratios of 95:5 to 80:20 (THS:CHS).

Compounds that are hydrophilic polymer viscosity enhancers, such as polvinyl alcohol or hydroxypropyl methyl cellulose, which also enhances the retention of liposomes on the tissues may be used. These compounds are used in about a 0.05–1.5% (w/v) concentration of the final preparation. When these compounds are used, they are added to the initial aqueous phase preparation (the pilocarpine-aqueous solution).

In the pilocarpine-THS preparations, several solutions may be used to adjust (titrate) the pH of the liposome solution; such titrants include, for example, sodium hydroxide or sodium citrate. The pH of the final preparation is about 2.0–6.5, more preferably about pH 4.0–5.0, most preferably about pH 4.5.

The acid requiring or acid tolerating bioactive agents (drugs) that may be used in the present invention are any of those that are stable at about pH 1.0–6.0. In particular, the invention is directed to the association of drugs containing an imidazole group, with liposomes, specifically pilocarpine, in which case the pH used in the method is preferably about 4.5. The amount of drug in the liposomes of the invention may vary with respect to the amount of lipid (THS) employed. For example, the drug to total lipid weight ratio may range from about 1:1 to about 1:3, but is preferably about 1:2. Preferably, the amount of pilocarpine (base equivalents) present in the final preparation is about 4% (w/v).

The lipid to stabilizer ratio may range from about 10:1 to 1:10, depending on the stabilizer used.

During preparation of the liposomes, organic solvents can be used to suspend the lipids. Suitable organic solvents are those with a variety of polarities and dielectric properties, which solubilize the lipids, and include but are not limited to chloroform, methanol, ethanol, and methylene chloride. As a result, solutions (mixtures in which the lipids and other components are uniformly distributed throughout) containing the lipids are formed. Solvents are generally chosen on the basis of their biocompatability, low toxicity, and solubilization abilities. In the present invention methylene chloride is the preferred organic solvent.

The liposome preparations resulting from the processes of the invention may be lyophilized or dehydrated according to standard procedures and stored until use, after which time they maybe rehydrated with an aqueous solution. Such a process requires the addition of a drying protectant prior to the drying process which maintains the integrity of the liposomes after rehydration. Such a protectant may be a saccharide such as, for example, sucrose, dextrose, maltose, or mannitol, and may be used in about 2–20% concentrations. For example, about 2.0, 3.0, 5.0, and 10.0% (w/v) mannitol can be used.

The THS compositions resulting from the processes of the present invention can be used therapeutically in mammals, including man, in the treatment of infections or conditions which require the sustained action of an associated drug in its bioactive form. Preferably, the excipients are in the form of liposomes having the bioactive agent associated with or entrapped therein. In the instant invention, the adrenergic drug pilocarpine is preferably used. The conditions that may be treated by the liposomes of the invention include but are not limited to disease states such as glaucoma, for example, those that can be treated with pilocarpine.

The mode of administration of the preparation may determine the sites and cells in the organism to which the compound will be delivered. The liposome composition of the present invention can be administered alone but will generally be administered in admixture with a pharmaceutically acceptable carrier or diluent selected with regard to the intended route of administration and standard pharmaceutical practice. The preparations of the invention may be intramuscular, oral, or topical, for example. In the administration of pilocarpine with the liposomes, the preparation is administered topically, e.g. ocularly.

For the oral mode of administration, the liposomes of this invention can be used in the form of tablets, capsules, losenges, troches, powders, syrups, elixirs, aqueous solutions and suspensions, and the like. In the case of tablets, carriers which can be used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols. When aqueous suspensions are required for oral use, the active ingredient is combined with emulsifying and suspending agents. If desired, certain sweetening and/or flavoring agents can be added.

For the topical mode of administration, the liposomes of the present invention may be incorporated into dosage forms such as gels, oils, emulsions, and the like. Such preparations may be administered by direct application as a cream, paste, ointment, gel, lotion or the like. The compositions of the present invention may also be used in cosmetic formulations. In such formulations, these compositions may be in the form of creams (e.g., moisturizing agents), lotions, gels, and the like.

The compositions of the present invention may be used for ocular administration in the treatment of ocular afflictions such as glaucoma. In such applications the compositions are, for example, ointments or droppable liquids and may be administered by ocular delivery systems known in the art such as applicators or eye droppers. The compositions can further contain mucomimetics such as hyaluronic acid, chondroitin sulfate, hydroxypropyl methylcellulose, or polyvinyl alcohol; and preservatives, such as sorbic acid EDTA or benzylkonium chloride, and the usual quantities of diluents and/or carrier materials.

For administration to humans in the curative treatment of disease states responding to pilocarpine therapy, the prescribing physician will ultimately determine the appropriate dosage for a given human subject, and this can be expected to vary according to the age, weight, and response of the individual as well as the nature and severity of the patient's disease. The dosage of the drug in liposomal form will generally be about that employed for the free drug. In some cases, however, it may be necessary to administer dosages outside these limits, and in such cases, the dosages will be determined by the treating physician.

The following examples are given for purposes of illustration and not by way of limiting the scope of the invention.

EXAMPLE 1

To 140 ml of sterile water for injection (USP) was added 0.11 gm of EDTA and 0.1 gm of sorbic acid. This solution was a heated briefly to completely dissolve, and then cooled. Pilocarpine HCl (9.42 gm) was then added to the aqueous solution and mixed, and the pH adjusted to pH 4.5 with NaOH. In another vessel, 20.4 gm of THS was added to 80 ml of methylene chloride. This solution was then added to 24.0 gm. of polyoxyethylene alkyl ether (Laureth-23) and the solution mixed. The aqueous solution containing the pilocarpine was then added to the THS solution in organic solvent, and the mixture vortically mixed vigorously for several minutes. The solution was then placed on a rotary evaporator in a water bath set at 40° C., and the solvent evaporated for 1 hour. After rotoevaporation, the solution was brought up to 200 ml volume with the addition of sterile water, the solutions pH adjusted to about 4.5 with NaOH, and the resulting liposome mixture divided into 5.0 ml aliquots and sealed in vials and stored at 4° C. The final preparation contained 10.2% THS, 4% pilocarpine, 12% stabilizer, and 0.05% (w/v) each of EDTA and sorbic acid.

EXAMPLE 2

The procedures and materials of Example 1 were followed, using polyoxyethylene alkyl ether (Laureth-12) as the stabilizer. The final concentrations were as follows: 12% Laureth-12, 4% pilocarpine, 12% THS, and 0.05% each of sorbic acid and EDTA.

EXAMPLE 3

The THS vesicles of Example 1 were examined under freeze-fracture electron microscopy as follows:

An aliquot (0.1–0.3 ul) of the 10% THS vesicle specimen was sandwiched between a pair of Balzers (Nashua, NH) copper support plates and rapidly plunged from 23° C. into liquid propane. Samples were fractured and replicated on a double replicating device in a Balzers freeze-fracture unit at a vacuum of $2 \times 10^{-6}$ mbar or better and at $-115°$ C. Replicas were floated off in 3N $HNO_3$, followed by washing in a graded series of Chlorox solutions. These were finally cleaned in distilled water and picked up on 300 Hex mesh copper grids (Polysciences, PA). Replicas were viewed on a Philips 300 electron microscope at a magnification of 22,000 times.

EXAMPLE 4

Aqueous and organic phases were prepared as follows:

A 5% (w/v) base equivalents pilocarpine HCl aqueous phase was prepared in sterile water for injection. A 10.2% (w/v) d-alpha-tocopherol acid succinate and a 12% (w/v) Laureth-12 solution was prepared in methylene chloride. One hundred ml of the organic phase was transferred to a 500 ml round bottom flask, and 80 ml of the aqueous phase was added. Sufficient sodium hydroxide (about 0.5–1.0 ml) was added to adjust the pH of the resulting solution to pH 4.5, as measured with pH indicator paper. The solvent was removed by vacuum evaporation (rotary evaporation in a water bath set at 35° C.), stopping periodically to adjust the pH to about 4.5 using NaOH or HCl. Following removal of the solvent, the volume was adjusted to 100 ml with sterile water. This resulted in a final pilocarpine HCl concentration of 4%.

EXAMPLE 5

The low pH pilocarpine liposomes with polyoxyethylene alkyl ether (Laureth-12) made by the process of Example 4 were tested for evidence of ocular pathology (toxicity) in the eyes of 3 female New Zealand White rabbits. Each rabbit received four hourly doses of 25 ul applied topically to the eye and were observed for evidence of toxicity for 72 hours. The classical Draize scoring system was used; the rabbits were observed for swelling, corneal or conjunctival damage, congestion, and general discomfort. The liposome preparations containing Laureth-12 were well tolerated.

What is claimed is:

1. A method of making an acidic pH tocopherol composition comprising a bioactive agent, said method comprising admixing in the presence of a stabilizer an organic phase, said organic phase comprising an organic acid having two carboxylic acid moieties, one of said carboxylic acid moieties having an ester linkage with a tocopherol, and the other carboxylic acid moiety being free or as a salt thereof, and an aqueous phase having an acidic pH, wherein the stabilizer allows the formation and/or maintenance of a bilayer state of the tocopherol in an acidic pH environment and is selected from the group consisting of polyoxyethylene alkyl ethers, polyoxyethylene esters, and octoxynol, and wherein the acidic pH is from about 2.0 to about 6.5.

2. The method of claim 1 wherein the pH is about 4.0–5.0.

3. The method of claim 2 wherein the pH is about 4.5.

4. A liposome composition comprising an organic acid having two carboxylic acid moieties, one of said carboxylic acid moieties having an ester linkage with a tocopherol, and the other carboxylic acid moiety being free or as a salt thereof, and a stabilizer at an acidic pH wherein the stabilizer allows the formation and/or maintenance of a bilayer state of the tocopherol in an acidic pH environment and is selected from the group consisting of polyoxyethylene alkyl ethers, polyoxyethylene esters, and octoxynol, and wherein the acidic pH is from about 2.0 to about 6.5.

5. A method of treating an ocular affliction comprising administering an ocular affliction-treating-effective amount of the composition of claim 4 to a subject in need of such treatment.

6. The composition of claim 4 wherein the tocopherol is alpha tocopherol hemisuccinate.

7. The composition of claim 6 wherein the composition additionally comprises a bioactive agent.

8. The composition of claim 7 wherein the bioactive agent requires or retains its biological activity at a pH between about 2.0 and about 6.5.

9. The composition of claim 8 wherein the bioactive agent requiring a pH from about 2.0 to about 6.5 has an imidazole group.

10. The composition of claim 9 where the bioactive agent is pilocarpine.

11. The composition of claim 4 wherein the polyoxyethylene alkyl ether has an average of about 4, about 12 or about 23 ethylene oxide units.

12. The composition of claim 11 wherein the pH is about 3.0–5.0.

13. The composition of claim 12 wherein the pH is about 4.5.

14. The composition of claim 13 wherein the composition additionally comprises preservative.

15. The composition of claim 14 wherein the preservative is selected from the group consisting of p-hydroxybenzoic acid esters, benzyl alcohol, benzalkonium chloride and sorbic acid.

16. The composition of claim 15 wherein the preservative is sorbic acid.

17. A method of treating an ocular affliction comprising administering an ocular affliction-treating-effective amount of the composition of claim 16 to a subject in need of such treatment.

18. A pharmaceutical composition comprising the composition of claim 16 and a pharmaceutically acceptable carrier or diluent.

19. A composition according to claim 4, comprising an ocular affliction treating amount of pilocarpine wherein the stabilizer is a polyoxyethylene alkyl ether having an average of about 12 ethylene oxide units.

20. A method of associating a bioactive agent requiring or tolerating a pH from about 2.0 to about 6.5 with liposomes comprising an organic acid having two carboxylic acid moieties, one of said carboxylic acid moieties having an ester linkage with a tocopherol, and the other carboxylic acid moiety being free or as a salt thereof, requiring physiological pH, comprising the step of admixing in the presence of a stabilizer an aqueous solution at a pH from about 2.0 to about 6.5 comprising the bioactive agent, with an organic solvent solution comprising the tocopherol in an organic solvent, wherein the stabilizer allows the formation and/or maintenance of a bilayer state of the tocopherol in an acidic pH environment and is selected from the group consisting of polyoxyethylene alkyl ethers, polyoxyethylene esters, and octoxynol.

21. The method of claim 20 wherein the pH is about 3.0–5.0.

22. The method of claim 21 wherein the pH is about pH 4.5.

23. The method of claim 22 comprising the additional step of removing the organic solvent.

24. The method of claim 20 wherein the organic solvent is methylene chloride.

25. The method of claim 20 wherein the aqueous solvent is water or buffer.

26. A method of associating a bioactive agent requiring or tolerating a pH from about 2.0 to about 6.5 with liposomes comprising an organic acid having two carboxylic acid moieties, one of said carboxylic acid moieties having an ester linkage with a tocopherol, and the other carboxylic acid moiety being free or as a salt thereof, requiring physiological pH, comprising the step of admixing an aqueous solution at a pH from about 2.0 to about 6.5 comprising pilocarpine HCl, with an organic solvent solution comprising alpha-tocopherol hemisuccinate and a stabilizer in methylene chloride, and removing the methylene chloride, wherein the stabilizer allows the formation and/or maintenance of a bilayer state of the tocopherol in an acidic pH environment and is selected from the group consisting of polyoxyethylene alkyl ethers, and polyoxyethylene esters, octoxynol.

27. The composition of claim 4 wherein the polyoxyethylene alkyl ester is polyoxyl stearate or d-alpha tocopheryl polyethylene glycol succinate.

* * * * *